US00PP27793P2

(12) United States Plant Patent
Graff

(10) Patent No.: US PP27,793 P2
(45) Date of Patent: Mar. 21, 2017

(54) ***HIBISCUS* PLANT NAMED 'XANTHE'**

(50) Latin Name: *Hibiscus rosa-sinensis*
Varietal Denomination: Xanthe

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 0 days.

(21) Appl. No.: 14/756,182

(22) Filed: Aug. 12, 2015

(51) Int. Cl.
*A01H 5/02* (2006.01)

(52) U.S. Cl.
USPC ..... Plt./257

(58) Field of Classification Search
USPC ..... Plt./257
See application file for complete search history.

(56) References Cited

PUBLICATIONS

UPOV hit on a hibiscus plant named 'Xanthe', QZ PBR 20150958, published Jun. 15, 2015.*

* cited by examiner

*Primary Examiner* — Anne Grunberg
(74) *Attorney, Agent, or Firm* — C. A. Whealy

(57) ABSTRACT

A new and distinct cultivar of *Hibiscus* plant named 'Xanthe', characterized by its upright, mounding and bushy plant habit; dark green-colored leaves; uniform and freely flowering habit; large golden yellow-colored flowers with dark red-colored centers; and excellent flower longevity.

3 Drawing Sheets

Botanical designation: *Hibiscus rosa-sinensis.*
Cultivar denomination: 'XANTHE'.

BACKGROUND OF THE INVENTION

The present invention relates to a new and distinct cultivar of *Hibiscus* plant, botanically known as *Hibiscus rosa-sinensis*, and hereinafter referred to by the name 'Xanthe'.

The new *Hibiscus* plant is a product of a planned breeding program conducted by the Inventor in Sabro, Denmark. The objective of the breeding program is to create new strong *Hibiscus* plants with attractive and long-lasting flowers.

The new *Hibiscus* plant originated from a cross-pollination in August, 2010 in Sabro, Denmark of a proprietary selection of *Hibiscus rosa-sinensis* identified as code designation GB 2008-4068, not patented, as the female, or seed, parent with a proprietary selection of *Hibiscus rosa-sinensis* identified as code designation GB 2007-0502, not patented, as the male, or pollen, parent. The new *Hibiscus* plant was discovered and selected by the Inventor as a flowering plant within the progeny of the stated cross-pollination in a controlled greenhouse environment in Sabro, Denmark in May, 2011.

Asexual reproduction of the new *Hibiscus* plant by vegetative terminal cuttings in a controlled greenhouse environment in Sabro, Denmark since September, 2011 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Xanthe'. These characteristics in combination distinguish 'Xanthe' as a new and distinct *Hibiscus* plant:

1. Upright, mounding and bushy plant habit.
2. Dark green-colored leaves.
3. Uniform and freely flowering habit.
4. Large golden yellow-colored flowers with dark red-colored centers.
5. Excellent flower longevity.

Plants of the new *Hibiscus* can be compared to plants of the female parent selection. Plants of the new *Hibiscus* differ primarily from plants of the female parent selection in the following characteristics:

1. Plants of the new *Hibiscus* are more vigorous than plants of the female parent selection.
2. Leaves of plants of the new *Hibiscus* are lighter green in color than leaves of plants of the female parent selection.

Plants of the new *Hibiscus* can be compared to plants of the male parent selection. Plants of the new *Hibiscus* differ primarily from plants of the male parent selection in the following characteristics:

1. Plants of the new *Hibiscus* and the male parent selection differ in flower bud color as plants of the male parent selection have green-colored flower buds.
2. Plants of the new *Hibiscus* and the male parent selection differ in flower color as plants of the male parent selection have light yellow-colored flowers.

Plants of the new *Hibiscus* can be compared to plants of the *Hibiscus rosa-sinensis* 'Boreas Yellow', disclosed in U.S. Plant Pat. No. 24,060. In side-by-side comparisons conducted in Sabro, Denmark, plants of the new *Hibiscus* differed from plants of 'Boreas Yellow' in the following characteristics:

1. Leaves of plants of the new *Hibiscus* were cordate in shape whereas leaves of plants of 'Boreas Yellow' were more reniform in shape.
2. Plants of the new *Hibiscus* and 'Boreas Yellow' differed in flower color as plants of 'Boreas Yellow' had bright yellow-colored flowers.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet is a side perspective view of a typical flowering plant of 'Xanthe' grown in a container.

The photograph on the second sheet is a close-up view of typical developing flower buds and a typical open flower of 'Xanthe'.

The photograph on the third sheet is a close-up view of a typical dissected flower of 'Xanthe'.

DETAILED BOTANICAL DESCRIPTION

The aforementioned photographs and following observations, measurements and values describe plants grown during the autumn and winter in 13-cm containers in a glass-covered greenhouse in Sabro, Denmark and under cultural practices typical of commercial *Hibiscus* production. During the production of the plants, day temperatures ranged from 20° C. to 25° C., night temperatures ranged from 19° C. to 21° C. and light levels ranged from 40 to 50 klux. Plants were pinched one time eight weeks after planting and plants were 26 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Xanthe'.

Parentage:

*Female, or seed, parent*.—Proprietary selection of *Hibiscus rosa-sinensis* identified as code number GB 2008-4068, not patented.

*Male or pollen parent*.—Proprietary selection of *Hibiscus rosa-sinensis* identified as code number GB 2007-0502, not patented.

Propagation:

*Type*.—By vegetative terminal cuttings.

*Time to initiate roots, summer*.—About three weeks at temperatures about 24° C.

*Time to initiate roots, winter*.—About four weeks at temperatures about 24° C.

*Time to produce a rooted young plant, summer*.—About eight weeks at temperatures about 24° C.

*Time to produce a rooted young plant, winter*.—About ten weeks at temperatures about 24° C.

*Root description*.—Medium in thickness, fleshy; color, close to 158A, actual color of the roots is dependent on substrate composition, water quality, fertilizer type and formulation, substrate temperature and physiological age of roots.

*Rooting habit*.—Freely branching; dense.

Plant description:

*Plant and growth habit*.—Container plant; upright, mounding and bushy plant habit; moderately vigorous growth habit.

*Branching habit*.—Freely branching habit with usually about five to eight lateral branches developing per plant; pinching enhances lateral branch development.

*Plant height*.—About 35 cm to 55 cm.

*Plant diameter* (*area of spread*).—About 30 cm to 50 cm.

Lateral branch description:

*Length*.—About 10 cm to 30 cm.

*Diameter*.—About 4 mm to 8 mm.

*Internode length*.—About 1 cm to 5 cm.

*Strength*.—Strong.

*Texture*.—Smooth, glabrous; becoming woody with development.

*Color, developing*.—Close to 147A.

*Color, developed*.—Close to N199A and 197A.

Leaf description:

*Arrangement*.—Alternate, single; numerous.

*Length*.—About 8 cm to 12 cm.

*Width*.—About 6 cm to 8 cm.

*Shape*.—Cordate.

*Apex*.—Acuminate.

*Base*.—Cordate, rounded.

*Margin*.—Irregularly serrate.

*Texture, upper surface*.—Smooth, glabrous; somewhat leathery.

*Texture, lower surface*.—Scattered pubescence; venation prominent.

*Luster, upper surface*.—Moderately glossy.

*Luster, lower surface*.—Matte.

*Venation pattern*.—Pinnate; arcuate.

*Color*.—Developing leaves, upper surface: Close to 137B. Developing leaves, lower surface: Close to 146B. Fully expanded leaves, upper surface: Close to 136A; venation, close to 137B. Fully expanded leaves, lower surface: Close to 137B; venation, close to 146A.

*Petioles*.—Length: About 2 cm to 5 cm. Diameter: About 2 mm. Texture, upper and lower surfaces: Smooth, glabrous. Color, upper and lower surfaces: Close to 146A.

Flower description:

*Flower arrangement*.—Flowers arranged singly at terminal leaf axils; uniform, continuous and freely flowering habit with numerous flowers developing per plant; flowers face mostly upright to slightly outwardly.

*Fragrance*.—None detected.

*Natural flowering season*.—Plants flower in the garden during the spring and summer or during periods of warm weather; in the greenhouse, plants can be flowered year-round; plants begin flowering about 12 to 16 weeks after pinching.

*Flower longevity*.—Excellent flower longevity, flowers last for about four to five days; flowers persistent.

*Flower diameter*.—About 16 cm to 20 cm.

*Flower length* (*height*).—About 10 cm to 11 cm.

*Flower buds*.—Rate of opening: Flowers buds open in about three days. Length: About 5 cm to 7 cm. Diameter: About 2 cm to 3 cm. Shape: Ovoid to elliptical. Color: Close to 160A.

*Petals*.—Arrangement: Five petals in a single whorl; petals imbricate. Length: About 10 cm to 11 cm. Width: About 8 cm to 9 cm. Shape: Fan-shaped. Apex: Rounded. Base: Attenuate. Margin: Entire; undulate. Texture, upper surface: Glabrous; rough with a velvety appearance. Texture, lower surface: Glabrous, rough with a satiny appearance. Luster, upper surface: Matte. Luster, lower surface: Slightly glossy. Color: When opening, upper surface: Close to 12A; towards the base, close to 53A. When opening, lower surface: Close to 16B. Fully opened, upper surface: Close to 13A; towards the base, close to 53A; with development, main color becoming closer to 12A. Fully opened, lower surface: Close to 16B; with development, color becoming closer to 8C.

*Sepals*.—Appearance: Five sepals fused into a campanulate-shaped calyx. Length: About 3 cm to 3.3 cm. Width: About 1 cm to 1.5 cm. Shape: Lanceolate. Apex: Acuminate. Margin: Entire. Texture, upper surface: Glabrous, rough. Texture, lower surface: Glabrous, smooth. Color, upper surface: Close to 144A. Color, lower surface: Close to 144B.

*Peduncles*.—Length: About 4 cm to 6 cm. Diameter: About 3 mm to 4 mm. Strength: Strong. Aspect: Mostly upright. Texture: Sparsely pubescent. Color: Close to 143A.

*Reproductive organs*.—Androecium: Stamen number: Numerous, more than 100. Filament length: About 1 cm. Filament color: Close to 11A. Anther shape: Rounded to ovate. Anther length: About 1 mm to 2 mm. Anther color: Close to 19A. Amount of pollen: Abundant. Pollen color: Close to 17A. Gynoecium: Pistil length: About 7 cm to 8 cm. Style length: About 5 cm to 6 cm. Style texture: Smooth, waxy. Style color: Close to 4B. Stigma appearance: Five-parted, rounded stigma pads. Stigma color: Close to 17C. Ovary color: Close to 149D.

*Seeds*.—Quantity produced per flower: About 1 to 15. Length: About 5 mm. Diameter: About 5 mm. Color: Close to 202A.

Temperature tolerance: Plants of the new *Hibiscus* have been observed to have tolerate temperatures from about 10° C. to about 40° C.

Pathogen & pest resistance: Plants of the new *Hibiscus* have not been observed to be resistant to pathogens and pests common to *Hibiscus* plants.

It is claimed:

1. A new and distinct *Hibiscus* plant named 'Xanthe' as illustrated and described.

* * * * *

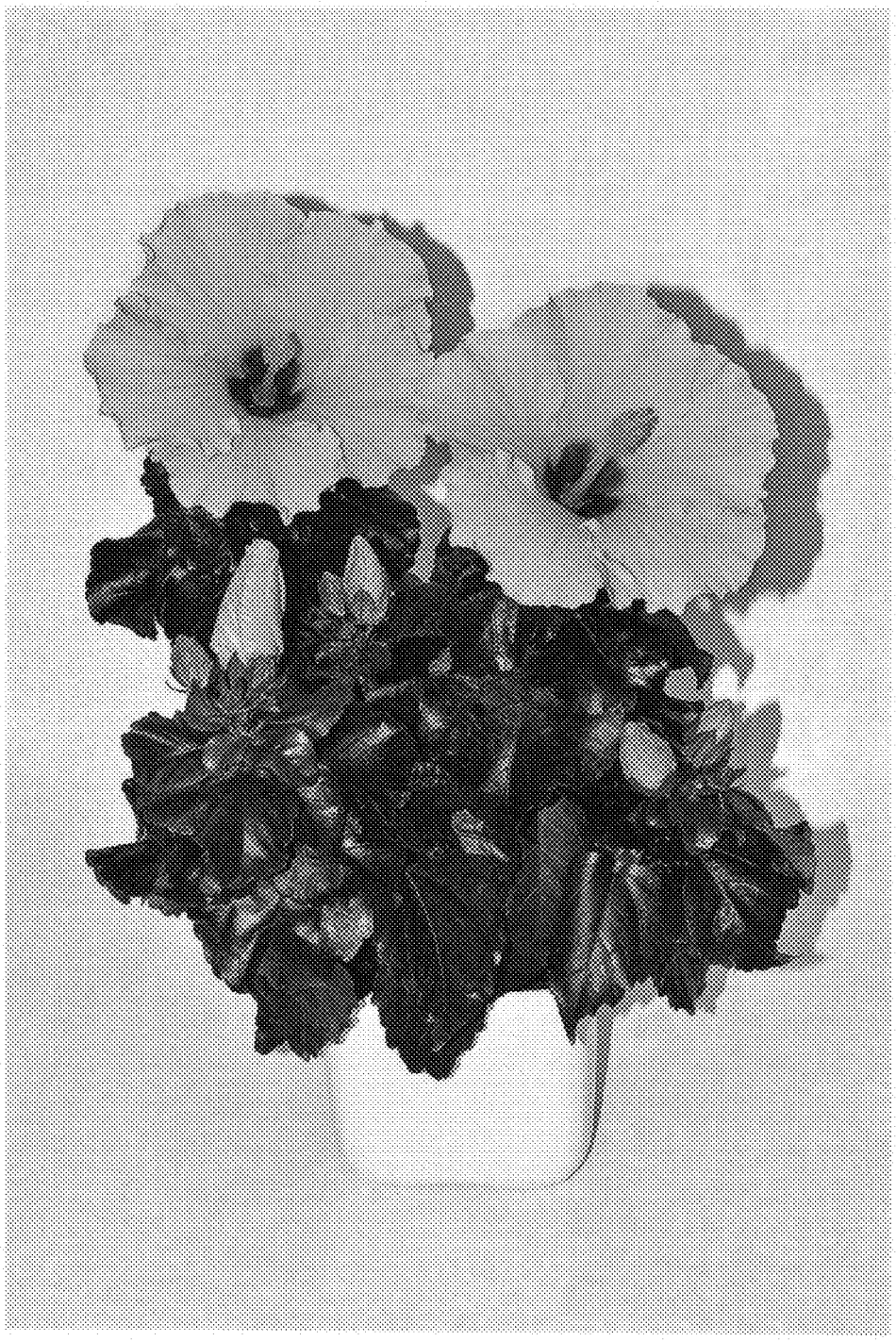

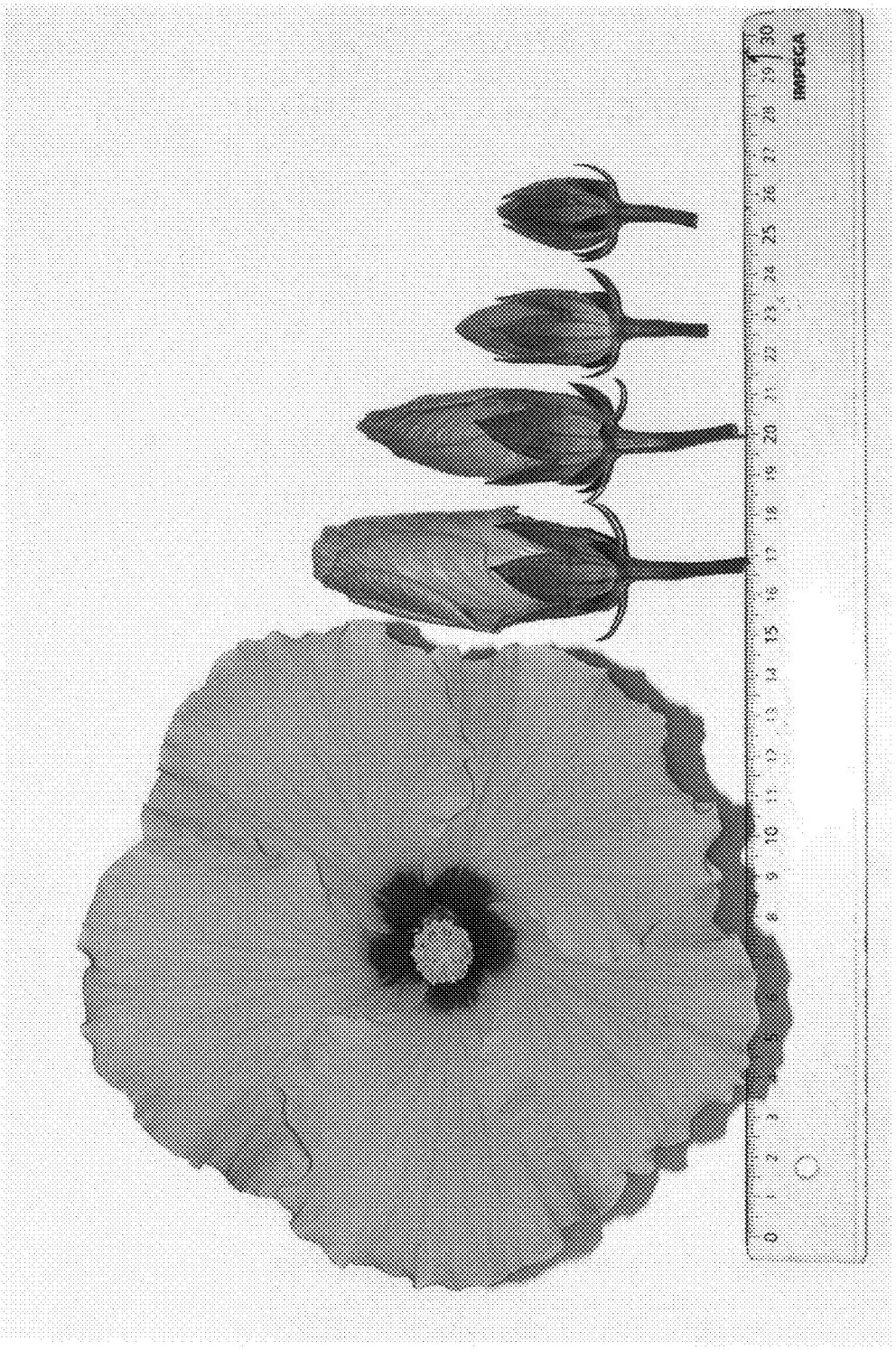
INCHES

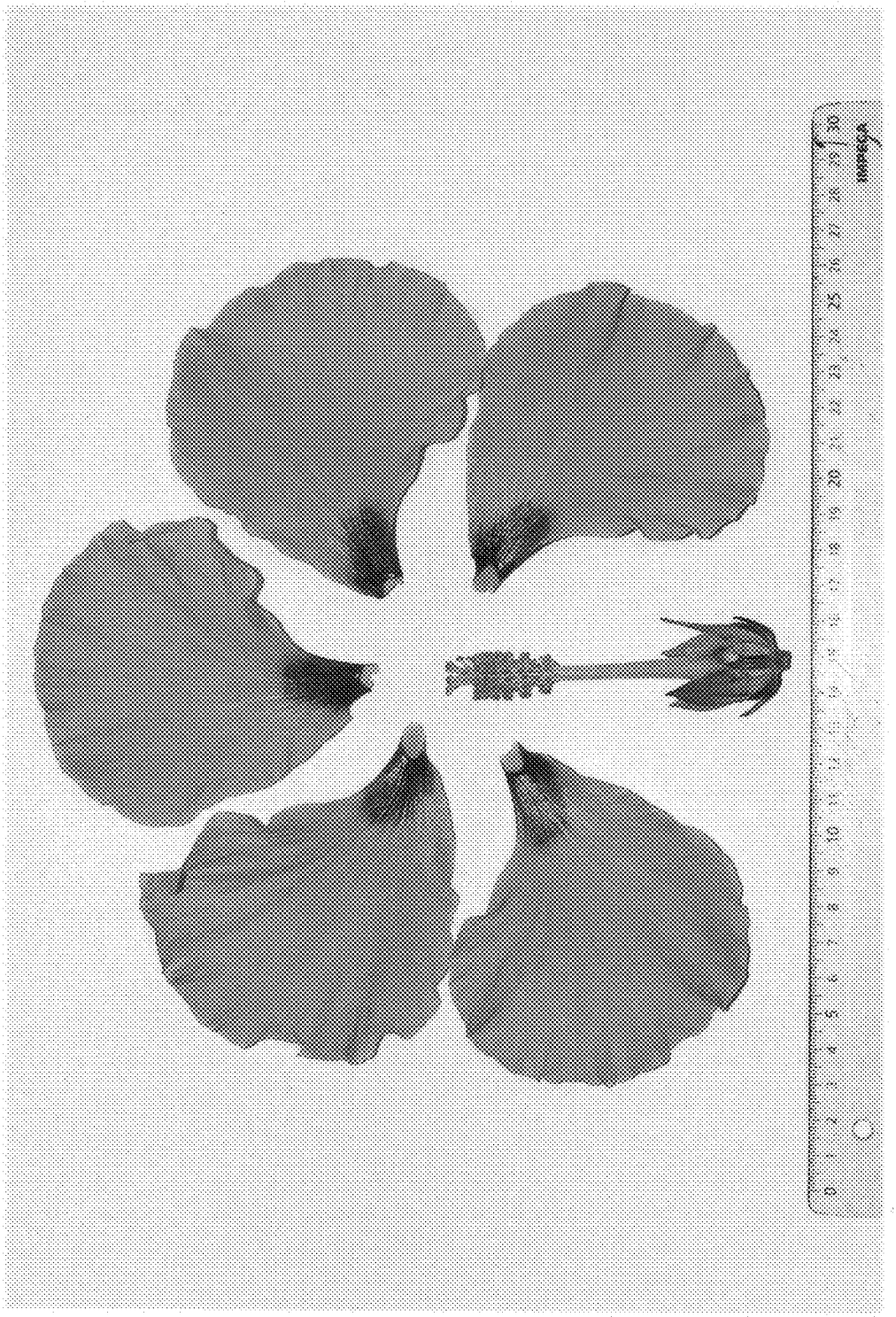
inches